United States Patent [19]
Giesler et al.

[11] Patent Number: 5,668,303
[45] Date of Patent: Sep. 16, 1997

[54] SENSOR HAVING A MEMBRANE AS PART OF AN ELECTROMECHANICAL RESONANCE CIRCUIT FORMING RECEIVER AND TRANSMITTER CONVERTER WITH INTERDIGITAL STRUCTURES SPACED APART FROM ONE ANOTHER

[75] Inventors: Thomas Giesler, Saarbruecken; J.-Uwe Meyer, St. Ingbert-Hassel, both of Germany

[73] Assignee: Forschung e.V Fraunhofer-Gesellschaft zur Foerderung der angewandten, Munich, Germany

[21] Appl. No.: 325,444

[22] PCT Filed: Apr. 21, 1993

[86] PCT No.: PCT/EP93/00969

§ 371 Date: Jan. 3, 1995

§ 102(e) Date: Jan. 3, 1995

[87] PCT Pub. No.: WO93/22669

PCT Pub. Date: Nov. 11, 1993

[30] Foreign Application Priority Data

Apr. 30, 1992 [DE] Germany ............... 42 14 451.5

[51] Int. Cl.⁶ ............... G01N 29/24; G01N 29/02
[52] U.S. Cl. ............... 73/24.06; 73/31.06; 73/54.41; 73/61.75; 73/61.79; 73/64.53; 310/324
[58] Field of Search ............... 73/24.06, 54.26, 73/54.41, 61.79, 31.06, 61.75, 64.53, 646, 647, 648; 310/313 B, 322, 324, 349, 313 R

[56] References Cited

U.S. PATENT DOCUMENTS

| | | | |
|---|---|---|---|
| 3,582,838 | 6/1971 | De Vries | 310/313 B |
| 3,676,721 | 7/1972 | Van Den Heuvel et al. | 310/313 B |
| 3,987,378 | 10/1976 | Onodera | 310/313 B |
| 4,409,570 | 10/1983 | Tanski | 310/313 A |
| 4,895,017 | 1/1990 | Pyke et al. | 13/24.06 |
| 5,446,330 | 8/1995 | Eda et al. | 310/313 R |
| 5,448,126 | 9/1995 | Eda et al. | 310/313 R |

OTHER PUBLICATIONS

*Sensors and Actuators B Chemical*, entitled "Acoustic Love-wave sensor for K+ concentration in H₂O solutions", vol. 87, No. 1/3, Mar. 1992, pp. 602–605.

"Effective Utilization of Acoustic Wave Sensor Responses: Simultaneous Measurement of Velocity and Attenuation" by S.J. Martin and A. J. Ricco (IEEE 1989 Ultrasonics Symposium, Oct. 3–6, 1989) pp. 621–625.

*Primary Examiner*—Hezron E. Williams
*Assistant Examiner*—Rose M. Finley
*Attorney, Agent, or Firm*—Evenson, McKeown, Edwards & Lenahan, P.L.L.C.

[57] ABSTRACT

Sensor provided with a thin membrane, capable of storing electrical charges, whose surface is in contact with the chemical, biological, and/or other physical parameters to be measured. The membrane is part of an electromechanical resonance circuit, operating with propagating acoustic waves. Provision is made opposite the membrane for converters, equipped with interdigital structures, to act as transmitter and receiver for the propagating acoustic plate waves. Each of the converters is equipped with interdigital structures that act as narrow band, filters. The transmitter converter and the receiver converter is arranged with a distance between them. The signal from the receiver converter is detected capacitively. A suitable electronic control and evaluation circuit or feedback is provided in addition between the output signal of the receiver converter and the transmitter converter. Finally, a DC voltage is applied between the membrane on the one hand and the transmitter converter and the receiver converter on the other. The voltage has an alternating voltage superimposed on it in the transmitter converter. The generation of the acoustic plate waves in transmitter converter is produced solely on the basis of electrostatic attractive force or excitation between interdigital structures of the transmitter converter and the membrane. The output signal of the receiver converter is additionally decoupled in a capacitive manner in such fashion that the vibration amplitude of the acoustic propagating plate waves is measured in the receiver converter by the capacitor formed by interdigital structures of the receiver converter and the membrane. Finally, the membrane and interdigital structures of the transmitter converter on the transmitter side and the membrane and interdigital structures of the receiver converter on the receiver side are arranged spaced apart from one another by a spatial distance in the form of a gap. They have no mechanically solid connection with one another. A dielectric in the form of a narrow gap is therefore formed such that movement of the membrane toward the interdigital structures is possible in the dielectric.

21 Claims, 4 Drawing Sheets

SENSOR HAVING A MEMBRANE AS PART OF AN ELECTROMECHANICAL RESONANCE CIRCUIT FORMING RECEIVER AND TRANSMITTER CONVERTER WITH INTERDIGITAL STRUCTURES SPACED APART FROM ONE ANOTHER

BACKGROUND AND SUMMARY OF THE INVENTION

The invention relates to a sensor and, more particularly, to a sensor provided with a thin membrane, capable of storing electrical charges, whose surface is in contact with the chemical, biological, and/or other physical parameters to be measured. The membrane is part of an electromechanical resonance circuit, operating with propagating acoustic waves. Provision is made opposite the membrane for converters, equipped with interdigital structures, to act as transmitter and receiver for the propagating acoustic plate waves. Each of the converters is equipped with interdigital structures that act as narrow band filters. The transmitter converter and the receiver converter is arranged with a distance between them. The signal from the receiver converter is detected capacitively. A suitable electronic control and evaluation circuit or feedback is provided in addition between the output signal of the receiver converter and the transmitter converter. Finally, a DC voltage is applied between the membrane on the one hand and the transmitter converter and the receiver converter on the other. The voltage has an alternating voltage superimposed on it in the transmitter converter.

Technical advancement has made it necessary to detect the presence of chemical or biochemical substances and to determine their concentrations, and to measure other physical parameters and their changes in the form of electrical signals. Sensors are used for this application. The sensor's theoretical purpose consists in the conversion of chemical and biochemical reactions, or the detection of the existence of or change in other physical parameters, into electrical signals, frequently accomplished with electronic means. The areas of application for such sensors include, for example, process monitoring, detection of impurities, performance of analyses, exhaust emissions monitoring, waterways monitoring, gas alarm systems, and medical technology, etc.

Mass-sensitive converters, also called gravimetric sensors, have been discussed for use as high-sensitivity sensors. This group of sensors reacts, for example, to the accumulation of, or a change in the accumulation of, the desired substance on the sensor on which a chemically active coating is provided for this purpose. The sensors are designed as an electromechanical resonance circuit. By using electrical oscillations and suitable feedback, the mechanical components of the sensor are set oscillating. If continuous waves are used in the resonator, the resonant frequency is determined by the phase velocity of the waves and possibly by the impressed wavelength.

Thus, for example, sensors are known that work with acoustic surface waves. A piezoelectric layer is used as the mechanical part of the resonator. Interdigital structures are evaporated onto the piezoelectric layer. The structures then, generate continuous acoustic surface waves under electric excitation that are emitted along the piezoelectric layer. Another interdigital structure applied to the piezoelectric layer acts as a receiver, receiving the acoustic surface waves emitted by the transmitter and converting them into an electrical signal. An electronic amplifier is provided between the transmitter and the receiver. The amplifier provides feedback between the receiver and the transmitter as well as compensation for losses. This produces an oscillating system that is free of damping.

The mechanical oscillator can be provided on one or both sides with a chemically active coating that is selected for the desired substance. The desired substance binds on the chemical coating of the substrate. This causes a change in mass or a change in the surface properties of the substrate. This in turn leads to a change in the resonant frequency or a change in the propagation rate of the waves. This causes a frequency shift in the resonant circuit, so that the deposition of the desired substance can be evaluated by an electrical signal.

The propagation rate of the acoustic surface waves is first determined by the material properties of the piezoelectric layer and, second, by their surface properties. Changing the properties of the oscillator changes the oscillator frequency. The sensitivity is inversely proportional to the wavelength and directly proportional to the frequency. Acoustic surface wave sensors can be operated at high frequencies of several hundreds of MHz. This gives them high sensitivity. Operating at high frequencies has disadvantages, however. Expensive, cumbersome, and trouble-prone electronics and a design using high-frequency criteria are required. A sensor of this kind radiates VHF waves, and the short wavelengths require very fine interdigital structures that pose manufacturing problems.

An important aspect of using acoustic surface wave sensors is the high propagation rate of the surface waves. Normally, it is far above the speed of sound in water or in other fluids. This results in a failure of the sensors when they are used in fluids. If the propagation rate of an acoustic surface wave is above the speed of sound of an ambient fluid, the wave dissipates in the fluid since the energy loss results in a sharp damping of the surface wave.

The use of surface wave sensors is therefore limited as a rule to gas or vapor detection.

Another class of gravimetric sensors is composed of sensors that work with acoustic plate waves. These acoustic plate waves propagate on a thin membrane and have much lower propagation rates at the same wavelength than those in sensors that use acoustic surface waves. The typical design of a sensor that uses acoustic plate waves relies on the structure of a resonant circuit with acoustic surface waves. A transmitter converter provided with interdigital structures and a receiver converter provided with interdigital structures are combined by means of an electronic amplifier with feedback and a thin membrane into an electromechanical resonator. The transmitter converter generates acoustic traveling plate waves that are picked up by the receiver converter. The Electromechanical conversion therefore involves a piezo effect. An aluminum layer is first evaporated onto a silicon nitride membrane; the aluminum layer then serves as a carrier for the piezoelectric layer made of zinc oxide, applied for example with electron-magnetron sputtering. Finally, the transmitter and receiver interdigital structures are evaporated onto the zinc oxide layer. The finger groups and finger numbers are designed so that one period (finger pair) corresponds exactly to a wavelength during operation at the resonant frequency. The wavelengths are between 10 and 1000 lm as a rule. This membrane serves as the mechanical part of the resonator and can be provided with a chemically active layer that selectively acts toward certain substances.

"Sputtering" of the zinc oxide layer produces compressive stress. In many cases, this causes waves in the membrane or breakage of the layer and similar problems. These problems increase with the thinness of the membrane. Therefore, it has not been previously possible to make any composite membrane thinner than about 3 1m. Since the sensitivity of the sensor increases inversely with the thickness of the membrane, the sensitivity of an acoustic plate wave sensor using the piezoelectric layer cannot be further increased.

Another research approach to a gravimetric sensor uses electrostrictive excitation of plate waves. This avoids "sputtering" of a piezoelectric layer. The structure is as follows:

A thicker aluminum layer is evaporated onto one side of a thin silicon nitride membrane. The interdigital structures of the transmitter converter and receiver converter are applied to the other side of the silicon nitride membrane. The acoustic plate waves are generated as follows: Between the fingers of the interdigital structures and the aluminum layer, a direct voltage is applied, superimposed on an alternating voltage to generate the acoustic plate waves. The electrostrictive effect is then in the form of a change in volume of the dielectric by polarization. The electric dipoles located sequentially in the direction of an outer electrical field exert an attractive force on one another in which the molecules approach one another until the elastic counterforces balance the electrical forces.

The mechanical stresses coupled in this fashion generate plate waves that propagate along the composite membrane. In the receiver converter, the advancing plate waves cause changes in thickness and in the dielectric constant of the nitride layer, resulting in turn in a change in the capacitance of the capacitors composed of an aluminum layer and fingers. This can be converted into an electrical signal. Electrical decoupling as a result of the change in thickness has merely been postulated but not demonstrated in practice.

Therefore, only relatively low amplitudes of the acoustic plate waves can be achieved by the electrostrictive method. The orders of magnitude of the idle voltage and the short-circuit current of the receiver converter are correspondingly small. Only a modest signal-to-noise ratio can be achieved.

Another problem with electrostrictive excitation methods is the high capacitance of the transmitter converter. Under the control of the typical exciting voltages, reactive powers in the range from 10 W appear, causing a large power loss in the control electronics and interfering with its miniaturization. Hence, the feasibility of a feedback resonator using this principle is very questionable.

Hence, there is needed a simple and economical acousto-gravimetric sensor suitable for mass production equipped with a membrane that is a part of an electromechanical resonator circuit, the circuit being suitable for measuring gaseous and liquid media, having a very high sensitivity, and also allowing the use of a membrane that is as thin as possible that also permits determination of the position of the sensor with high resolution.

These needs are met according to the present invention by a sensor provided with a thin membrane, capable of storing electrical charges, whose surface is in contact with the chemical, biological, and/or other physical parameters to be measured. The membrane is part of an electromechanical resonance circuit, operating with propagating acoustic waves. Provision is made opposite the membrane for converters, equipped with interdigital structures, to act as transmitter and receiver for the propagating acoustic plate waves. Each of the converters is equipped with interdigital structures that act as narrow band filters. The transmitter converter and the receiver converter is arranged with a distance between them. The signal from the receiver converter is detected capacitively. A suitable electronic control and evaluation circuit or feedback is provided in addition between the output signal of the receiver converter and the transmitter converter. Finally, a DC voltage is applied between the membrane on the one hand and the transmitter converter and the receiver converter on the other. The voltage has an alternating voltage superimposed on it in the transmitter converter. The generation of the acoustic plate waves in transmitter converter is produced solely on the basis of electrostatic attractive force or excitation between interdigital structures of the transmitter converter and the membrane. The output signal of the receiver converter is additionally decoupled in a capacitive manner in such fashion that the vibration amplitude of the acoustic propagating plate waves is measured in the receiver converter by the capacitor formed by interdigital structures of the receiver converter and the membrane. Finally, the membrane and interdigital structures of the transmitter converter on the transmitter side and the membrane and interdigital structures of the receiver converter on the receiver side are arranged spaced apart from one another by a spatial distance in the form of a gap. They have no mechanically solid connection with one another. A dielectric in the form of a narrow gap is therefore formed such that movement of the membrane toward the interdigital structures is possible in the dielectric.

The advantages of the present invention consist, in particular, in that the generation of acoustic propagating plate waves takes place at the transmitter solely by the electrostatic method, while at the receiver end the input and decoupling of the output signal are detected purely by capacitive means. This makes it possible for the dielectric between the membrane and the interdigital structures on the transmitter and receiver side to consist of air, so that undamped oscillating movements of the membrane are possible and a dielectric is chosen such that these oscillating movements of the membrane remain possible. The function of the sensor according to the present invention is ensured in both gaseous and liquid media.

Other advantages consist in the fact that by separating the interdigital structures of the transmitter converter and the receiver converter from the membrane, the acoustic plate waves can be generated on any membranes or foils. By separating these interdigital structures and the membrane, various converters can be produced. As a result, the possibility of developing position sensors is created. Extremely thin membranes can be used in the electromechanical resonant circuit, since when a pure metal membrane is used, for example, there is no problem of two-layer materials working against each other because of different coefficients of expansion. The very thin membranes also permit an extremely high sensitivity for the sensor according to the invention.

In the electrostatic method, the acoustic plate waves can reach amplitudes of about 800 Å. In the receiver converter, the idle voltage is higher than in the electrostrictive method. This results in a much higher output voltage and a very high signal-to-noise ratio for the electrostatic method in contrast with the electrostrictive method. In terms of both the order of magnitude of the idle voltage and the short-circuit current, as well as the noise distance, the electrostatic method according to the invention is superior to the electrostrictive method. It offers far greater reserves for additional electronic processing, and capacitive parasitic effects and interference have much less of an effect because of the higher level.

Other objects, advantages and novel features of the present invention will become apparent from the following detailed description of the invention when considered in conjunction with the accompanying drawings.

receiver

Figure 4:
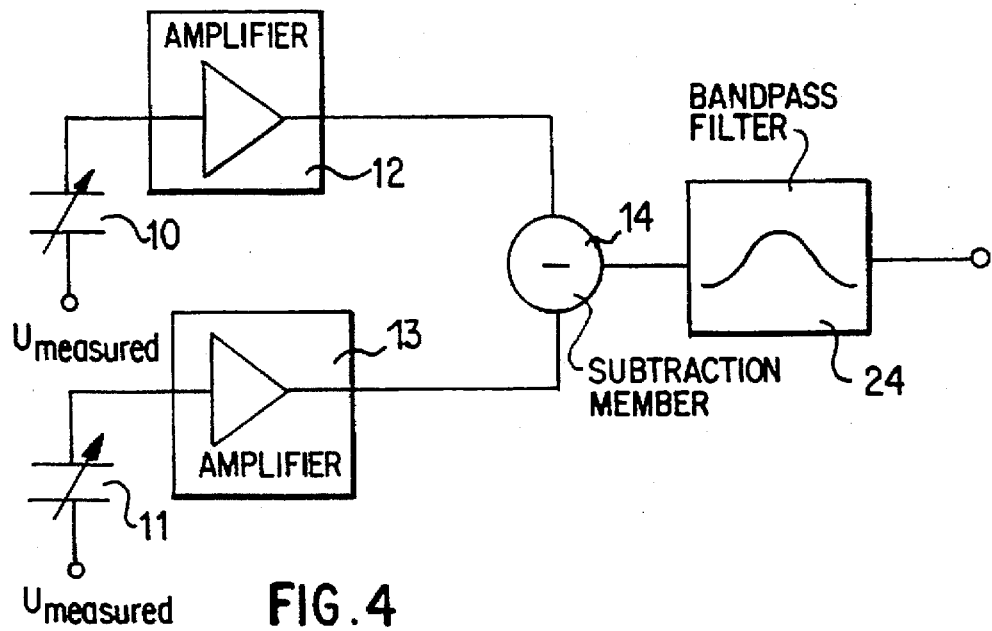
Figure 5:
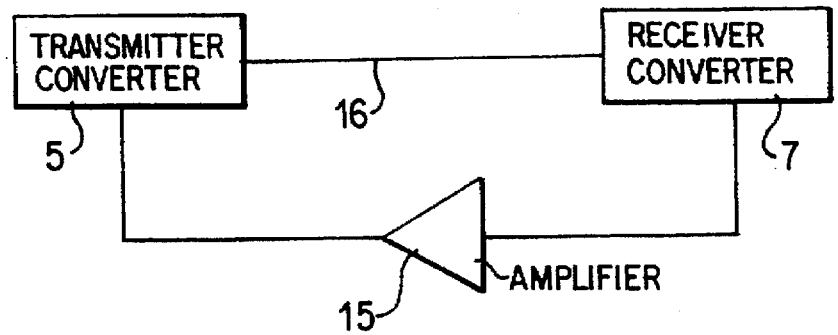
Figure 6:
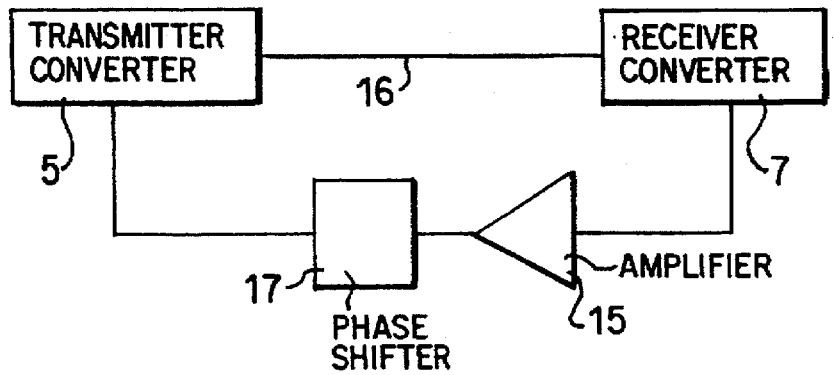
Figure 7:
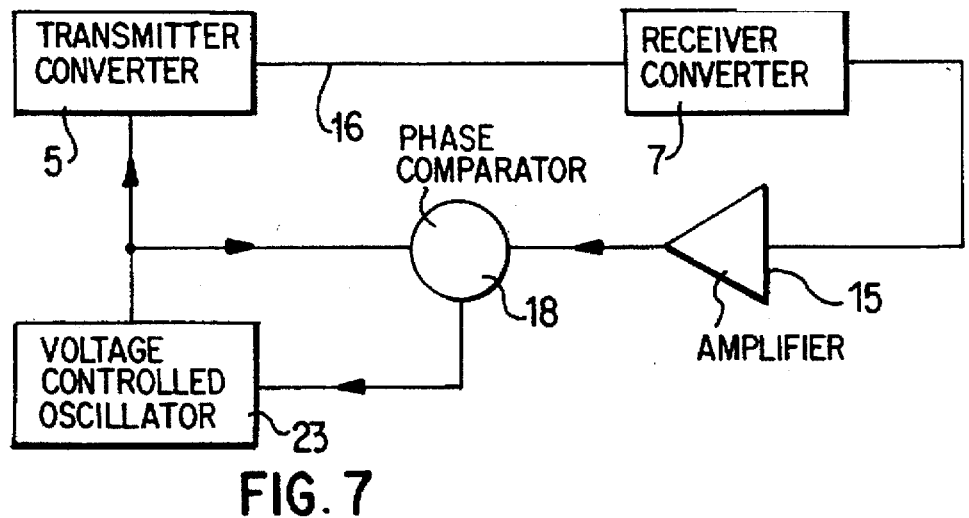
Figure 8:
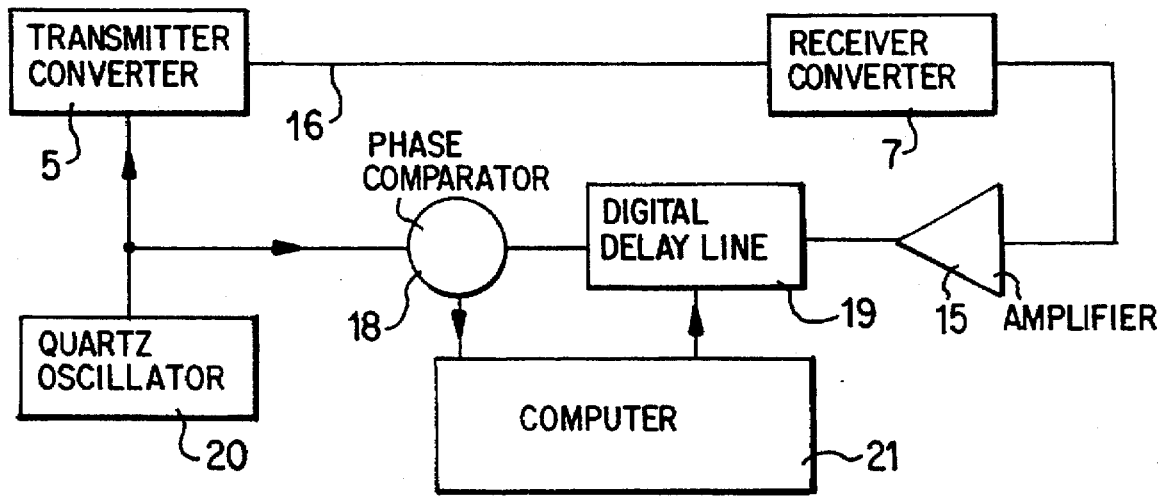
Figure 9:
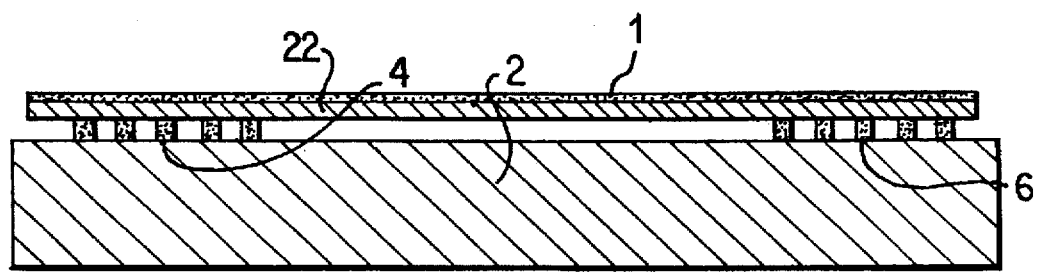
Figure 10:
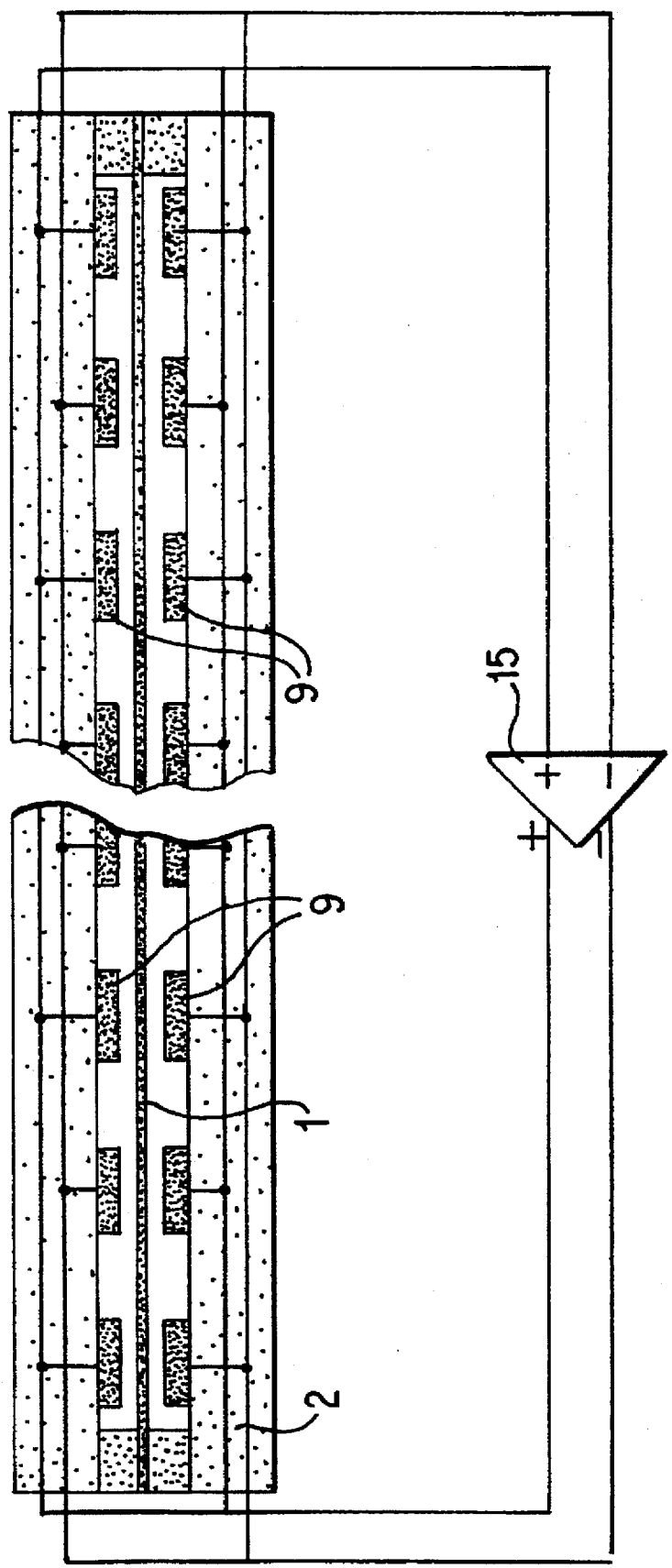

FIG. 4 is a schematic block diagram of the converter;

FIG. 5 is a schematic block diagram of the electromechanical resonance circuit for measured value evaluation using direct feedback;

FIG. 6 is a schematic block diagram of the electromechanical resonance circuit for measured value evaluation with direct feedback, expanded by one phase shifter;

FIG. 7 is a schematic block diagram of the electromechanical resonance circuit for measured value evaluation with indirect feedback via PLL;

FIG. 8 is a schematic block diagram of the electromechanical resonance circuit for measured value evaluation by means of phase measurement;

FIG. 9 illustrates an arrangement of the membrane with a solid in the gap with the interdigital structures of the transmitter and receiver converters; and FIG. 10 illustrates a symmetric arrangement of the interdigital structures on both sides of the membrane.

DETAILED DESCRIPTION OF THE DRAWINGS

Figure 1:
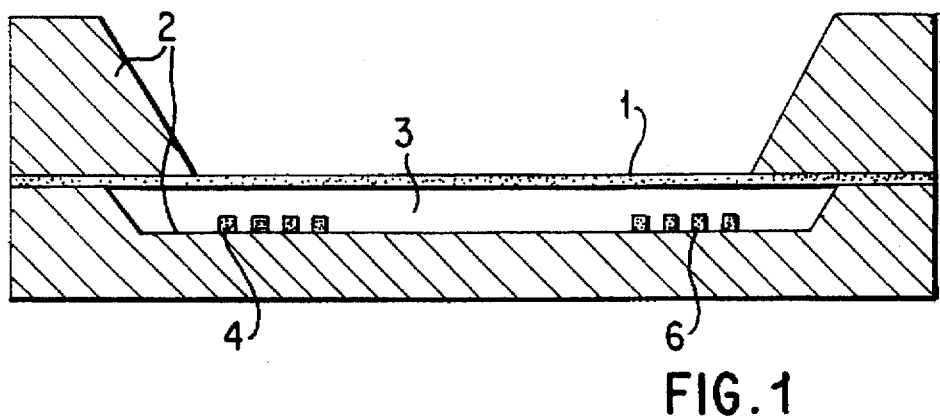
FIG. 1 is a cross-sectional view of the sensor according to the invention with a homogeneous metal membrane.

FIG. 1 is a schematic diagram of a first embodiment of the sensor with high sensitivity according to the present invention [with high sensitivity]. A membrane 1 is mounted on a support 2. Membrane 1 and the interdigital structures 4 of transmitter converter 5 (FIG. 5) are on the transmitter side while membrane 1 and the interdigital structures 6 of receiver converter 7 (FIG. 5) are on the receiver side, each separated from one another by a spatial distance in the form of a narrow gap 3. For this purpose, narrow gap 3 is designed as a dielectric in such fashion that movement of membrane 1 toward interdigital structures 4 and 6 is possible in the dielectric. Transmitter converter 5 and receiver converter 7 are arranged with a distance between them, so that the plate waves can pass through membrane 1.

Figure 2:
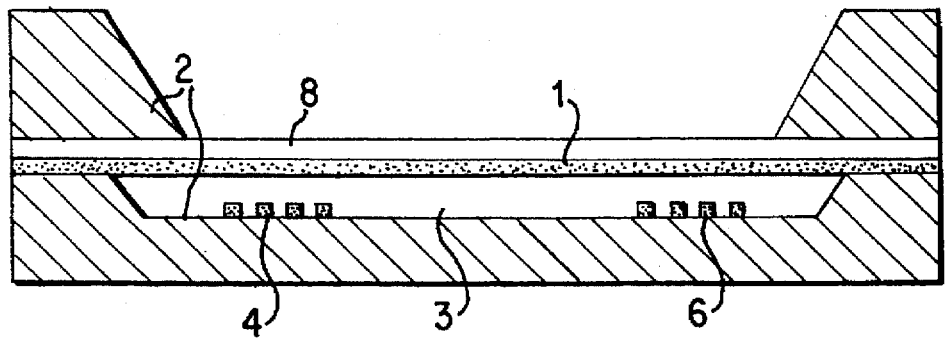
FIG. 2 is a cross-sectional view of the sensor according to the invention with a membrane made of a thin nitride layer and an applied metal layer.

Membrane 1 consists for example of a homogeneous metal foil alone. The thickness of the membrane can vary in the lm range, for example by micromechanical manufacture. Aluminum or any other metal foil suitable for such a purpose may be used. Metal membrane 1, however, can also consist of a metal layer applied to a thin nonconducting silicon nitride layer 8; see FIG. 2. Membrane 1, 8 can be provided with a chemically active coating on the side facing away from interdigital structures 4 and 6. This chemically selective coating produces a recipient for special molecules or chemicals that then are deposited on the foil during wetting. The sensitivity of the sensor or the resonator circuit to be described in greater detail below is influenced by the mass of the membrane. If a substance is deposited on an applied chemically active coating or directly on the membrane, the membrane mass changes, resulting in a shift in the resonant frequency. The sensitivity of such a resonator to mass deposits is inversely proportional to the density and thickness of the entire membrane. For example, if the material for the membrane is specified, the weight per unit area can only be influenced by the thickness of the membrane. The sensor sensitivity therefore increases inversely with membrane thickness. Thus, a membrane that is as thin as possible is desirable to achieve high sensitivity.

Figure 3:
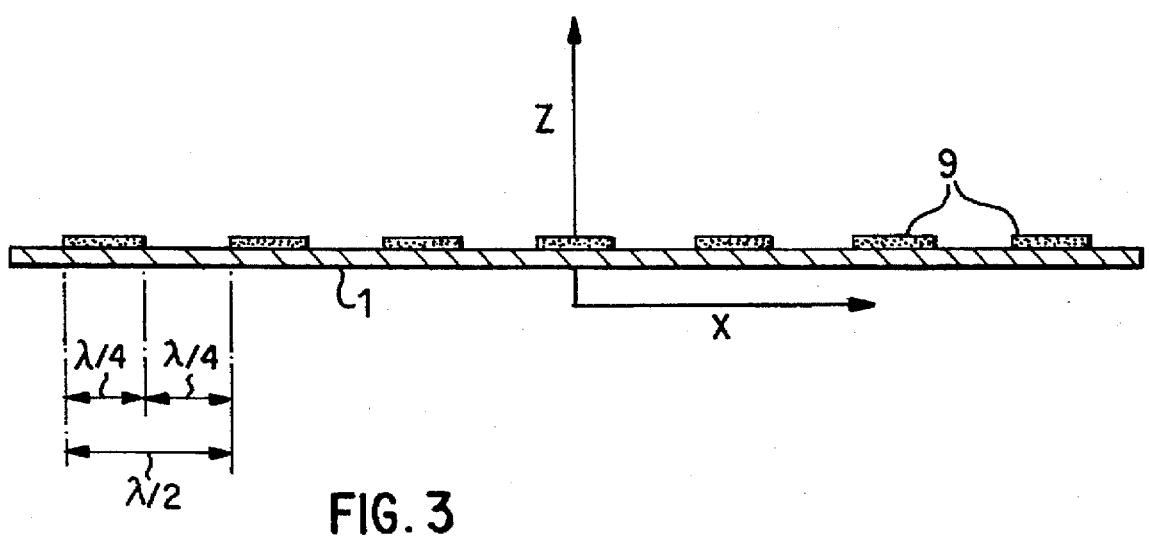
FIG. 3 is a partial view in section of the interdigital structures of a transmitter or receiver converter.

Interdigital structures 4 and 6 are used to transmit and receive acoustic propagating plate waves. Because of their selective filtration properties, they are suited for determining the wavelength and mode of the plate waves. To allow the sensor to function in liquids, a propagation rate that is as low as possible is desirable, for which purpose the $A_0$ mode is best suited. In this mode, the propagation rate decreases to zero as the plate thickness decreases. The interdigital structures of both transmitter converter 5 and receiver converter 7 consist of two finger groups each of suitably selected finger length, finger width, and finger number, with the number of fingers influencing the quality of the filter. The two filter groups of the transmitter and receiver converters are arranged so they are pushed into one another. The complete converter in each case consists of n fingers and transmits acoustic plate waves along membrane 1 in the positive and negative x directions; see FIG. 3. Each of the n fingers in turn constitutes an elementary converter. All such elementary converters are arranged at intervals of k/2 and oscillate with a phase shift of 180° to achieve coherent transmission. The two finger groups of the electrostatic transmitter converter are therefore controlled phase shifted by 180°. The amplitudes are then added in coherent wave superimposition.

A DC voltage is applied between membrane 1 and interdigital structures 4 and 6 of the transmitter and receiver converters. In transmitter converter 5, an alternating voltage is superimposed on interdigital structures 4, which then serves to excite acoustic plate waves. In those positions in which converter fingers are located, the membrane is charged with a harmonically alternating pressure and oscillates accordingly. Each of the individual elementary converters transmits plate waves symmetrically in both directions. These then overlap and form the resultant plate wave that leaves the interdigital structures of the transmitter on both sides. Generation of acoustic propagating plate waves therefore takes place in the transmitter converter by means of the membrane and the interdigital structures, solely due to electrostatic attractive force or excitation. This takes place precisely during detection and decoupling of the signal of the receiver converter in a purely capacitive fashion. The two interdigital structures of the transmitter and receiver converters can have the same design, but a dissimilar arrangement with different numbers of fingers is also possible if necessary.

Just as interdigital structures 4 and membrane 1 form capacitors, capacitors are also formed in the receiver converter by membrane 1 and its interdigital structures 6. In these capacitors, the acoustic propagating plate waves arriving from the transmitter are directly decoupled with their oscillation amplitude.

Since each interdigital structure consists of two finger groups arranged interlocked with one another, both the transmitter and the receiver converter contain two capacitors formed by membranes and finger groups. The output signals from the receiver converter are amplified, then subtracted from one another and band-limited. Because of the k/2 arrangement of the individual fingers, the two signals from the receiver converter are added, with a phase shift of 180°, and the disturbing parasitics appear. A block diagram of the receiver converter is shown in FIG. 4. It consists of the two capacitors 10 and 11 formed by the two finger groups of the interdigital structures with the membrane, amplifiers 12 and 13, subtraction member 14, and possibly bandpass filter 24, which limits the noise bandwidth of electronic components 12, 13, and 14. Both a transmitter and receiver converter likewise operate as narrow-band filters or resonators for a frequency that is determined by the material properties of the membrane.

The phase velocity of the acoustic plate waves can be used as a measurement parameter for an electrical signal to be evaluated. If plate waves with a firmly established frequency are transmitted from the transmitter converter over the delay line, plate waves with the same fixed frequency can be received at the receiver converter. The delay line consists of the membrane and all of the factors that influence the membrane, for example the mass deposition on the membrane, the density of the medium surrounding the membrane, and other parameters that affect the membrane. If the phase velocity of the acoustic propagating plate waves changes, the mutual phase position between the transmitter converter and receiver converter changes as well. This phase drift thus forms the output parameter of the sensor.

In order to obtain a sensor with the output parameters of the frequency, an amplifier 15 is connected between the receiver converter 7 and the transmitter converter 5; see FIG. 5. The amplification of amplifier 15 must be chosen to be sufficiently high so that the losses of the transmitter converter, the delay line from the membrane, and the receiver converter can be offset. If this is achieved, the circuit oscillates at its typical resonant frequency which is then influenced and changed by the phase velocity.

If a phase shifter 17 (FIG. 6) is additionally wired in series with amplifier 15 in the feedback branch, by changing the phase rotation of the phase shifter the frequency can be adjusted to the center frequency of the transmitter and receiver converters or to the transmission maximum. In selecting amplifier 15 and phase shifter 17, it is important to ensure a minimal phase drift in the electronic components, since this would lead to frequency drift and hence to a falsification of the measured value. This evaluation circuit requires only a small number of electronic components.

In direct feedback, the oscillation frequency of the electromechanical resonator is roughly determined by the filter center frequency of the converter. The exact determination is made by the phase condition between the transmitter and receiver which is specified by the oscillation condition. When the time constant of the delay line changes, the frequency changes as well, since the phase position is superimposed. The frequency is therefore the output parameter from the sensor and can be recorded very easily in a quasi-digital manner.

The block diagram in FIG. 7 avoids direct feedback between the receiver converter and transmitter converter by adding a phase lock loop. With the aid of a voltage-controlled oscillator 23, a phase comparator 18, and a lowpass filter, the phase condition between the transmitter converter 5 and the receiver converter 7 is maintained. The output amplitude of voltage-controlled oscillator 23 is constant, so that constant amplitudes can be obtained during buildup as well as in normal operation. Moreover, disturbing parasitics and noise in the amplifier circuit are not reamplified and coupled into the acoustic wave line. The voltage-controlled oscillator and phase comparator can thus be made digital and computer-controlled, permitting a further improvement in the system properties.

Another advantage of the circuit shown in FIG. 7 is the high degree of constancy of the transmitter signal. By measuring the amplitude of the receiver converter signal, a direct derivation of the damping of the acoustic line is possible, which is advantageous in many sensor applications, for example density measurement.

FIG. 8 shows a block diagram for direct measurement of the phase position between the transmitter converter 5 and receiver converter 7, making it possible to measure changes in the phase velocity. A digital phase comparator 18 compares the phase position of quartz oscillator 20, acting as a reference oscillator, with the phase position of receiver converter 7. If a fixed phase ratio exists, the phase comparator delivers a signal to a computer 21. The computer is then able to control the phase position on the phase comparator through a digitally-controllable delay member consisting of a delay line 19. The circuit design shown in the block diagram in FIG. 8 has no analog components. With the quartz oscillator, it has a highly accurate reference, constant excitation amplitude, and the possibility for digital measurement by computer-controlled successive approximation of the phase position.

The membrane, which consists of a homogeneous metal foil or a nitride layer made of silicon with an evaporated metal layer, is attracted by the DC voltage applied between the membrane and the interdigital structures in the direction of the digital structures. If the voltage difference between the membrane and the interdigital structures is too high, the membrane could come to rest on the interdigital structures. To avoid this bending effect, the membrane can be given an internal tensile stress during manufacture. If these tensile stresses are large enough, bending of the membrane by the electrostatic force onto the interdigital structures is prevented. The reflection of the acoustic plate waves at the edge of the membrane can be prevented by making a part of the sides of the membrane curved and/or bevelled. This prevents standing waves or other disturbances from being reflected by the edges of the membrane.

Additional measures will now be described that can prevent bending of the membrane up to the counterelectrode of the interdigital structures. Thus it is possible, for example, that a rough insulating layer can be provided to generate an air cushion in the narrow gap 3 between membrane 1 and interdigital structures 4 and 6 of transmitter and receiver converters 5 and 7. A hermetically sealed air space can also be provided in the narrow gap between the membrane and the interdigital structures of the transmitter and receiver converters, with this hermetically sealed air space being filled with the prevailing atmospheric pressure.

In addition, a dielectric solid supporting structure with a high acoustic impedance can be provided in the narrow gap between the membrane and the interdigital structures of the transmitter and receiver converters. Liquid can also be added to narrow gap 3 as a dielectric between the membrane and the interdigital structures of the transmitter and receiver converters. The gap can then be designed as a hermetically sealed fluid gap. The fluid is incompressible and can provide the necessary counterforce against bending of the membrane. The liquid abutting the membrane reduces the effective membrane mass and hence the sensor sensitivity. Therefore, this version is suited only for sensors intended for use in liquids, since in that case the other side of the membrane is also covered by liquid. With this arrangement there is a maximum halving of the sensitivity of the sensor by having both sides wetted by liquid.

If a solid body with a very high acoustic impedance is placed in gap 3 between membrane 1 and interdigital structures 4 and 6, the plate waves can propagate without significant energy loss without the sensor sensitivity being sharply reduced thereby, and a low compressibility is achieved as well. A modified sensor shape for this purpose is shown in FIG. 9. It would be especially suitable for gas sensors. A freely applied membrane 1 rests on an acoustically soft dielectric 22 that in turn rests on interdigital structures 4 and 6 of transmitter and receiver converters 5 and 7. These in turn are mounted on support 2. An arrangement of this kind has the advantage of substrate-independent membrane manufacture, while external bilateral membrane coatings can be provided and the membranes can be easily replaced. The membrane is completely stress-free and no changes in membrane tension are produced by thermal housing or substrate expansion. Atmospheric pressure variations cannot affect the membrane and high field strengths can be achieved, corresponding to high amplitudes. The membrane must either be made of homogeneous metal or be provided with a metal coating. Since the membrane must be kept at a fixed DC voltage potential, a connection to the control electronics is necessary, possibly by a corresponding electrical connection using a bond wire.

In all of the above-mentioned embodiments for the dielectric, the gap or dielectric is made the same between the membrane and the interdigital structures of the transmitter and receiver converters. By separating the membrane from the interdigital structures of the transmitter and receiver converter, acoustic plate waves can be generated on any membranes and foils and it is also possible then to displace the interdigital structures, in both the transmitter converter and the receiver converter. The sensor can then be used for position measurements. It can also be used for measurements of material properties, for example modulus of elasticity, Poisson coupling, bending stiffness, thickness, and weight per unit area of foils and other membranes in manufacturing quality control.

Another opportunity for preventing membrane bending as a result of electrostatic forces can be seen in FIG. 10. The symmetric arrangement of the interdigital structures shown here on both sides of the membrane 1 for both the transmitter and the receiver converters prevents the development of a unilateral static force on the membrane. As a result, there is no bending and the membrane is nevertheless freely accessible on both sides. To permit gas exchange with the environment, small openings can be etched in the two electrode supports. This arrangement is not sensitive to pressure fluctuations. The decouplable signal is increased by doubling the number of electrodes. The arrangement, however, is only suitable for gas sensors or sensors in nonconducting liquid since the membrane is under the influence of an electrostatic field on both sides.

What is claimed is:

1. Sensor having a thin membrane, capable of storing electrical charges, a surface of said membrane being in contact with chemical, biological, and/or other physical parameters to be measured, with the membrane being part of an electromechanical resonance circuit operating with propagating acoustic plate waves, comprising:

converters, provided opposite the membrane, equipped with interdigital structures to act as transmitter and receiver for said propagating acoustic plate waves, each of said converters being equipped with interdigital structures that act as narrow band filters, with the transmitter converter and receiver converter being arranged with a distance between them, and with a signal from the receiver converter being detected capacitively, one of an electronic control and evaluation circuit and feedback being provided between an output signal of the receiver converter and the transmitter converter, wherein a DC voltage is applied between the membrane on the one hand and the transmitter converter and the receiver converter on the other hand, said voltage having an alternating voltage superimposed on it in the transmitter converter, wherein the generation of the propagating acoustic plate waves in said transmitter converter is produced solely on the basis of electrostatic attractive force or excitation between said interdigital structures of said transmitter converter and said membrane, further wherein said output signal of said receiver converter is additionally decoupled in a capacitive manner in such fashion that a vibration amplitude of the propagating acoustic plate waves is measured in said receiver converter by a capacitor formed by said interdigital structures of said receiver converter and said membrane, and wherein said membrane and said interdigital structures of said transmitter converter on the transmitter side and said membrane and said interdigital structures of said receiver converter on the receiver side are arranged spaced apart from one another by a spatial distance in the form of a gap, there being no mechanically solid connection with one another, and a dielectric in the form of narrow gap being formed such that movement of said membrane toward said interdigital structures occurs in the dielectric.

2. Sensor according to claim 1, wherein said membrane is made solely of a homogeneous metal foil.

3. Sensor according to claim 1, wherein said membrane is made of a metal layer applied to a thin nonconducting layer.

4. Sensor according to claim 3, wherein said thin nonconducting layer is made of silicon nitride and said metal layer is one of evaporated and sputtered.

5. Sensor according to claim 1, wherein said membrane is provided with an internal tensile stress.

6. Sensor according to claim 1, wherein said interdigital structures of the transmitter and receiver converter are provided on two supports on both sides of the membrane, and wherein individual fingers of said interdigital structures are opposite the two sides of the membrane, both the individual fingers arranged side by side on the supports and the individual fingers located opposite on both sides of the membrane are excited with constantly changing positive and negative voltage.

7. Sensor according to claim 1, wherein said dielectric in the narrow gap between the membrane and the interdigital structures of the transmitter and receiver converters consists of air.

8. Sensor according to claim 1, wherein a rough insulating layer is provided in the narrow gap between the membrane and the interdigital structures of the transmitter and receiver converters to generate an air cushion.

9. Sensor according to claim 9, wherein a hermetically sealed air gap is provided in the narrow gap between the membrane and the interdigital structures of the transmitter and receiver converters.

10. Sensor according to claim 1, the hermetically sealed air gap is filled with the prevailing atmospheric pressure.

11. Sensor according to claim 1, wherein a dielectric solid supporting structure with a high acoustic impedance is added in the narrow gap between the membrane and the interdigital structures of the transmitter and receiver converters.

12. Sensor according to claim 1, wherein said dielectric in the narrow gap between the membrane and the interdigital structures of the transmitter and receiver converters consists of fluid.

13. Sensor according to claim 1, wherein the membrane is surrounded on both sides by fluid.

14. Sensor according to claim 1, wherein a hermetically sealed liquid is provided in the narrow gap between the membrane and the interdigital structures of the transmitter and receiver converters.

15. Sensor according to claim 1, wherein individual fingers in both interdigital structures of the transmitter and receiver converters are arranged at a spacing of half the resonance wavelength, and in that said two interdigital structures in the transmitter and receiver converters are controlled with a phase shift of 180° with alternating voltage.

16. Sensor according to claim 1, wherein said interdigital structures of the transmitter and receiver converters are made the same.

17. Sensor according to claim 1, wherein the dielectric between the membrane and the interdigital structures of the transmitter and receiver converters is made the same.

18. Sensor according to claim 1, wherein the interdigital structures of at least one of the transmitter and receiver converter are made displaceable.

19. Sensor according to claim 1, wherein the membrane is provided on the side facing away from the interdigital structures with a chemically active and selective coating.

20. Sensor according to claim 1, wherein at least one of the membrane and the interdigital structures and the dielectric are made micromechanically.

21. Sensor according to claim 1, wherein an edge of the membrane is so shaped that a portion of the sides of the membrane is at least one of curved and bevelled for acoustic reflection suppression.

* * * * *